United States Patent [19]

Schumacher et al.

[11] Patent Number: 4,519,961
[45] Date of Patent: May 28, 1985

[54] PRODUCTION OF DRY POWDERS OF SUBSTANCES WHICH ARE SENSITIVE TO OXIDATION

[75] Inventors: Horst Schumacher, Bobenheim; Paul Grafen, Weisenheim, both of Fed. Rep. of Germany

[73] Assignee: BASF Aktiengesellschaft, Fed. Rep. of Germany

[21] Appl. No.: 413,085

[22] Filed: Aug. 30, 1982

[30] Foreign Application Priority Data

Sep. 5, 1981 [DE] Fed. Rep. of Germany ....... 3135329

[51] Int. Cl.³ .................... A61J 5/00; B01J 13/02; B05D 7/00
[52] U.S. Cl. .................... 264/4.6; 252/522 A; 424/35; 424/36; 424/37; 427/213; 427/213.35; 514/725
[58] Field of Search ............ 42.7/213, 213.35; 264/4.6; 424/37; 252/522 A

[56] References Cited

U.S. PATENT DOCUMENTS

| | | | |
|---|---|---|---|
| 2,756,177 | 7/1956 | Cannalonga et al. | 264/109 |
| 2,897,119 | 7/1959 | Dunn | 424/35 X |
| 3,202,731 | 8/1965 | Grevenstuk et al. | 427/213 X |
| 3,445,563 | 5/1969 | Clegg et al. | 424/37 X |
| 3,499,962 | 3/1970 | Wurzburg et al. | 264/4.6 X |
| 3,890,433 | 6/1975 | Oishi et al. | 424/37 |
| 3,962,384 | 6/1976 | Cannalonga et al. | 264/7 |
| 4,262,017 | 4/1981 | Kuipers et al. | 424/284 |

FOREIGN PATENT DOCUMENTS

| | | |
|---|---|---|
| 0005529 | 11/1979 | European Pat. Off. |
| 1035319 | 12/1961 | Fed. Rep. of Germany |
| 389505 | 4/1960 | Switzerland |
| 420817 | 4/1960 | Switzerland |
| 431252 | 4/1961 | Switzerland |
| 488455 | 5/1966 | Switzerland |

Primary Examiner—Richard D. Lovering
Attorney, Agent, or Firm—Keil & Weinkauf

[57] ABSTRACT

A process for pulverizing substances which are sensitive to oxidation, in particular oily substances, by dispersing oil-soluble substances, e.g. vitamins, carotinoids, pharmaceutically active compounds or aromas, in an aqueous solution of a film-forming colloid, which constitutes the continuous phase of the dispersion, with the addition of one or more substances from the group comprising the mono-, di- and polysaccharides, atomizing the dispersion, in a spray tower, in the presence of a spraying assistant and collecting the resulting particles in a fluidized bed, wherein, as the spraying auxiliary, a hydrophobic silica or a metal salt of a higher fatty acid is introduced above the fluidized bed and distributed uniformly in the spraying space, at a temperature at which the colloid of the atomized particles has not yet solidified, and the assistant-laden particles, colloid material of which essentially has not yet gelatinized, is collected in a fluidized bed, and dried therein in a conventional manner.

6 Claims, 4 Drawing Figures

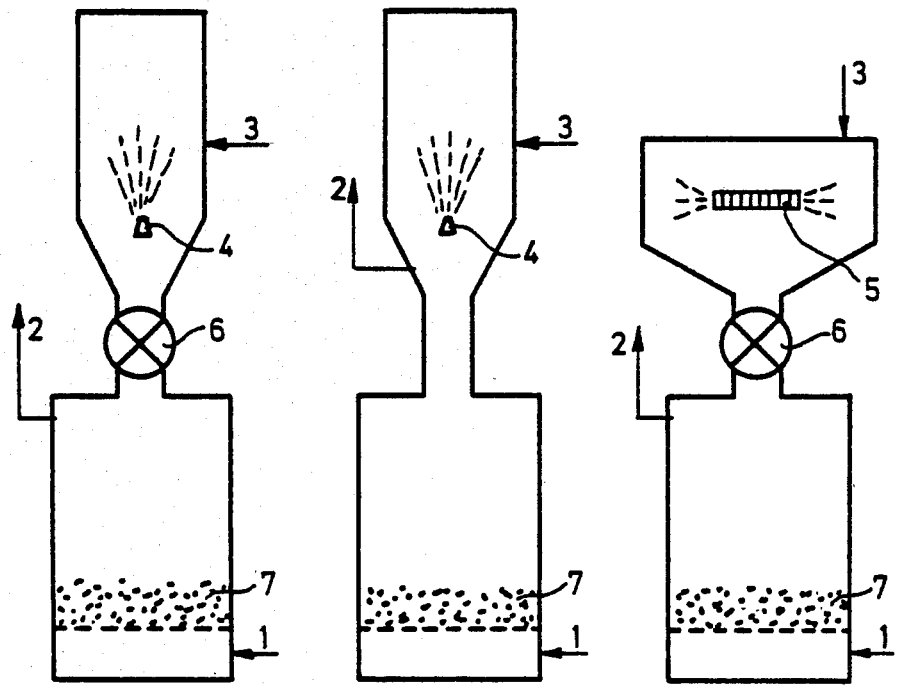
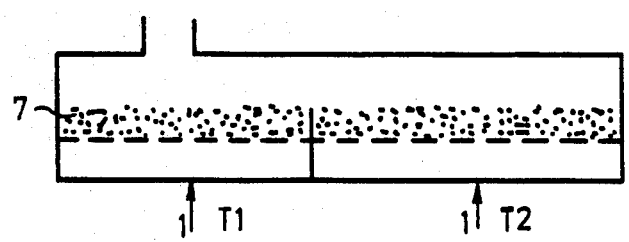
FIG.1  FIG.2  FIG.3
FIG.4

PRODUCTION OF DRY POWDERS OF SUBSTANCES WHICH ARE SENSITIVE TO OXIDATION

The present invention relates to an improved process for the production of dry powders of, in particular, oily substances which are sensitive to oxidation, by atomizing a dispersion of the oily substances in a colloid, in the presence of a spraying assistant.

There are various spraying processes for converting substances which are sensitive to oxidation, e.g. vitamins A, E and D or carotinoids, into dry, free-flowing powders which are protected against oxidation. The powder should consist of particles having a well formed surface and a size of 100–600 μm, the maximum of the particle size distribution being at about 250 μm. Powders having this particle size distribution ensure adequate protection of the active compound, and the number of particles per unit weight is still high enough so that during further processing in the pharmaceutical, food and feedstuff industries it is possible to obtain homogeneous mixtures of these products with other substances, with food or with feedstuffs.

In the conventional processes which produce powders having the desired properties, for example, an aqueous dispersion of the oily active ingredient in a film-forming colloid from the group comprising the proteins, e.g. gelatin and casein, or the polysaccharides, e.g. pectins, or gum arabic or cellulose compounds, with or without a sugar or sugar alcohol, e.g. glucose, lactose, sucrose or sorbitol, and in most cases with the addition of an antioxidant, an emulsifier and/or a preservative, is prepared, the dispersion is atomized, and the resulting particles are then dried.

In particular, it has been disclosed, for example in German Pat. No. 1,035,319, that a dispersion of an oily vitamin in a large excess of a starch powder with a water content below 8% can be atomized. The dry starch powder removes sufficient water from the particles so that they solidify. A great disadvantage of this process is that about 15% of the amount of starch remains adhering to the surface of the particles, and the excess starch must be separated off so that, after it has been dried, it may be recycled to the process.

In another process, which is described in Swiss Pat. No. 488,455, the starch is replaced by a mixture of water-absorbing inorganic substances and inorganic substances which do not absorb water, in order to eliminate the danger of explosion which arises from the presence of the finely divided starch. For optimum results, as much as a 20-fold excess of the carrier powder is required in this case.

According to the process described in Swiss Pat. No. 389,505, an active ingredient dispersion is sprayed into a cooled, gaseous medium, in which the particles reside until they sodidify. As a rule, this requires falling distances of from 12 to 15 m, at temperatures below room temperature, and, for economic reasons, this process can be carried out in many cases only with high-melting colloids.

Furthermore, Swiss Pat. No. 420,817 describes a process in which the particles which have been sprayed into cooled air are prevented from adhering to one another by spraying them on to a specially coated belt which moves rapidly with respect to the spray nozzle, and removing the solidified particles from the belt by means of a scraping or brushing system, and then drying them.

Finally, the process described in Swiss Pat. No. 431,252 may be mentioned, in which the dispersion is sprayed, at a temperature at which the particles solidify, into a carrier powder composed of a mixture of solidified and solidifying particles with a metal salt of a higher fatty acid as a lubricant. The bottom of the collecting chamber must consist of a specially constrcuted sieve system. In this case, also, the particles are finally dried.

All these processes are unsatisfactory.

It is an object of the invention to provide a process by means of which active ingredients which are sensitive to oxidation, in particular oily active ingredients, can be converted into finely divided powders in a simple manner.

We have found that this object is achieved, in accordance with the invention, by dispersing an oil-soluble substance, e.g. a vitamin, a carotinoid, a pharmaceutical active compound or an aroma, in an aqueous solution of a film-forming colloid, which constitutes the continuous phase of the dispersion, with the addition of one or more substances from the group comprising the mono-, di- and polysaccharides, atomizing the dispersion, in a spray tower, in the presence of a spraying auxiliary, and collecting the resulting particles in a fluidized bed, wherein, as the spraying assistant, from 0.02 to 0.15 times the amount by weight, based on the dispersion, of a hydrophobic silica or a metal salt of a higher fatty acid, for example of 16 to 18 carbon atoms, or a mixture of such salts with silica, is introduced (in the absence of significant amounts of other conventional spraying auxiliaries, e.g. starch powder) above the fluidized bed and distributed uniformly in the spraying space, at a temperature at which the colloid which is present in the atomized particles and which may or may not gelatinize has not yet solidified, and the assistant-laden particles, the colloid material of which essentially has not gelatinized, is collected in a fluidized bed, and dired therein in a conventional manner.

Preferred colloids are gelatins, for example from 70 to 200 Bloom, or casein. The amount of colloid used is as a rule from 5 to 50% by weight, based on the end product, where the dispersion contains from 30 to 70% by weight of water. To prepare the dispersion, the film former, followed by the active ingredient, are dispersed in a sugar solution at from 50° to 70° C. The dispersion is then atomized.

The form of the atomizing unit has no decisive effect on the product. Thus, for example, nozzles or rapidly rotating atomizer discs may be used. The temperature of the dispersion to be atomized is not a critical parameter. It is conventionally from 60° to 90° C., giving viscosities of from 50 to 1,200 mpas (60° C.) in the case of the colloids mentioned. It is important that when atomization takes place the particles come into contact with the hydrophobic spraying assistant, which is introduced in finely divided form directly into the spraying zone.

The advantages of the novel process are that the temperature in the spraying space need no longer be so low that the dispersion of the active ingredient forms a gel, and that it is unecessary to add large amounts of auxiliary powders in order to make the droplets solidify. Using the novel process, for example, active ingredient dispersions which do not solidify even at refrigerator temperatures (+4° C.) may be atomized at from 25° to 30 ° C. The amount of spraying assistant required for this purpose is only from 0.02 to 0.15 times the amount of the dispersion.

Suitable hydrophobic spraying auxiliaries are silanized silicas, as described in Die Mühle und Mischfuttertechnik 114 (1977), 3, and metal salts of higher fatty acids of 16 to 18 carbon atoms, e.g. calcium stearate and magnesium stearate, or mixtures of these salts with silica. As a result of directly introducing the particles into the spraying zone, they are substantially free of mechanical load, to which they would be subjected, for example, by a carrier-containing fluidized bed. The thin hydrophobic film of the spraying assistant, which film is produced during the spraying, stabilizes the particles sufficiently to prevent them from combining when they come into contact with one another before they have solidified, and thereby permits the particles to be dried directly in a downstream fluidized bed dryer.

The spraying assistant is fed in, advantageously above the atomizing unit, together with about 5 m³ of air per kg of spraying assistant, at room temperature, and is then atomized.

BRIEF DESCRIPTION OF DRAWINGS

For a description by schematic representation of the type apparatus which may be employed in practicing the present invention, reference is made to the accompanying drawings in which:

FIGS. 1 to 3 are apparatuses in which a powder can be dried batchwise.

FIG. 4 shows an apparatus for continuous drying.

In these figures, (1) is the dry air feed, (2) is the dry air outlet, (3) is the spray assistant feed (injector), (4) is an atomizing nozzle, (5) is a whirler, (6) is a star feeder, (7) is the fluidized bed, $T_1$ is a temperature from 20° to 40° C. and $T_2$ is a temperature from 40° to 90° C.

The examples which follow illustrate the novel process:

EXAMPLE 1

(arrangement according to FIG. 1)

14 parts of gelatin (100 Bloom) are stirred into a solution of 56.4 parts of glucose syrup (80% solids content) in 49 parts of water, and left to swell for 1 hour. Thereafter, 13.6 parts of corn starch are added, and the mixture is emulsified at 61°–63° C. with 24.9 parts of vitamin A acetate (2.21 million IU/g) stabilized with ethoxy-quin. The resulting dispersion, which has a viscosity of 104 mPas at 60° C., is atomized at from 80° to 90° C. and under a pressure of 60 bar. 10.5 kg/hour of hydrophobic silica (Sipernat D17) are introduced into the spraying zone during spraying. Spraying is carried out at a rate of 162 kg/hour of dispersion. After drying in a fluidized bed at 28°–38° C., a powder of the following composition is obtained:

content 572,000 IU/g
sieve analysis in accordance with

| DIN 500 μm | 3.5% |
|---|---|
| 400 | 9.8% |
| 250 | 38.9% |
| 160 | 35.0% |
| 125 | 8.5% |
| 100 | 2.7% |

EXAMPLE 2

(arrangement according to FIG. 3)

The procedure described in Example 1 is followed, except that the dispersion, having a viscosity of 1,196 mPas (60° C.), is atomized at 62° C. under atmosperic pressure, using an atomizing disc (5) at 24,300 rpm. Spraying is carried out at a rate of 77 kg/hour of dispersion, 4.5 kg/hour of hydrophobic silica (Sipernat D 17) being employed. The vitamin content of the powder is 591,000 IU/g, and the sieve analysis in accordance with ASTM is as follows:

| No. 35 | 0.2% |
|---|---|
| 40 | 1.4% |
| 45 | 12.3% |
| 60 | 46.0% |
| 80 | 30.2% |
| 120 | 7.5% |
| 140 | 1.4% |

EXAMPLE 3

(arrangement according to FIG. 1)

19.4 parts of gelatin (100 Bloom) are stirred into a solution of 53 parts of water and 7.9 parts of sucrose, and left to swell for 1 hour. Thereafter, the mixture is heated to 62° C., emulsified with 6.8 parts of vitamin A acetate (2.71 million IU/g), and the emulsion stabilized with butylhydroxytoluene. The dispersion has a viscosity of 127 mPas (60° C.) and is atomized at from 80° to 90° C. under a pressure of 50 bar, by means of a one-material nozzle (4). During spraying, 22 kg/g of calcium stearate (Ceasit levissimum) are fed into the spraying chamber, together with a stream of air. The dispersion is sprayed at a rate of 260 kg/hour. The product is dried in a fluidized bed at 28° C. The vitamin content of the powder is 514,000 IU/g. Sieve analysis in accordance with ASTM gives:

| No. 30 | <1% |
|---|---|
| 35 | 5.7% |
| 40 | 15.7% |
| 45 | 21.2% |
| 60 | 28.7% |
| 80 | 17.8% |
| 120 | 7.9% |
| 140 | 2.0% |

EXAMPLE 4

(arrangement according to FIG. 2)

2.8 parts of acid-coagulated casein (110 mesh) are stirred into a solution, at 63° C., of 15 parts of water and 39.5 parts of glucose syrup (80% solids content). The pH is brought to 7 by the addition of 10% strength sodium hydroxide solution. Thereafter, the mixture is emulsified with 0.25 part of fatty acid monoglyceride and 12.8 parts of vitamin A acetate (2.18 million IU/g), stabilized with ethoxyquin. The dispersion, having a viscosity of 202 mPas at 60° C., is atomized at from 80° to 90° C. under a pressure of 50 bar, by means of a single-material nozzle. 18.5 kg/hour of hydrophobic silica (Sipernat D 17) are introduced into the spraying zone during spraying. The dispersion is sprayed at a rate of 150 kg/hour. The product is dried in a fluidized bed dryer at from 25° to 33° C. in the course of 7 hours. The vitamin content of the powder is 542,000 IU/g; sieve analysis in accordance with ASTM gives:

| No. 35 | 0.2% |
|---|---|
| 40 | 0.2% |
| 45 | 1.1% |
| 60 | 24.1% |
| 80 | 49.3% |
| 120 | 17.8% |
| 140 | 4.2% |

EXAMPLE 5

(arrangement according to FIG. 2)

9 parts of gelatin are stirred into a solution of 50 parts of water and 25 parts of dextrose, 9 parts of starch are added, and the mixture is then heated to 62° C. 7.5 parts of a cantaxanthin mixture with vegetable oil and ethoxyquin (active compound content 70%) are dispersed in this mixture, the viscosity of the dispersion being 163 mPas at 60° C. The dispersion is introduced into the spraying space at 62° C., 11 kg/hour of hydrophobic silica (Sipernat D 17) being metered in, and is sprayed at a rate of 295 kg/hour. Drying is carried out in a fluidized bed at from 28° to 30° C. The resulting dry powder contains 9.8% of active ingredient and gives the following ASTM sieve analysis:

| No. 35 | 0.2% |
|---|---|
| 40 | 0.8% |
| 45 | 5.9% |
| 60 | 43.7% |
| 80 | 31.2% |
| 120 | 11.5% |
| 140 | 3.5% |

We claim:

1. A process for converting an oxygen-sensitive, oil soluble substance into a dry, free-flowing, oxygen-insensitive powder, which comprises:
   (a) dispersing said oxygen-sensitive, oil soluble substance in an aqueous solution which contains a film-forming colloid and one or more compounds selected from the group consisting of a mono-, di-, and poly-saccharide to form a dispersion wherein said colloid constitutes the continuous phase;
   (b) atomizing said dispersion within the spraying zone of a spray tower to form discrete particles therefrom;
   (c) causing said particles, as they form, to contact a hydrophobic spray assistant selected from the group consisting of silanized silica, a metal salt of a higher fatty acid and mixtures thereof in the absence of significant amounts of starch powder, with the newly formed particles being at a temperature during such contact which precludes solidification; said contact being effected by maintaining a uniform distribution of said spray assistant in the spraying zone of said spray tower during atomization of said dispersion therein to form said particles, with the spray assistant being supplied to the spraying zone in an amount of from about 0.02 to 0.15 parts by weight based on the weight of said dispersion;
   (d) collecting said particles laden with said hydrophobic spray assistant in a fluidized bed downstream from the spraying zone of said spray tower with said bed being maintained in a fluidized state by an upwardly directed flow of dry air; and
   (e) causing said particles to solidify and dry in said fluidized bed by means of the upward flow of dry air through the bed.

2. A process as claimed in claim 1, wherein gelatin or casein is used as the colloid.

3. A process as claimed in claim 1, wherein the air fed to the fluidized bed for the purpose of drying is removed below the spraying zone of the spray tower.

4. The process in accordance with claim 1, wherein said oxygen-sensitive, oil soluble substance is a vitamin.

5. The process in accordance with claim 1, wherein said oxygen-sensitive, oil-soluble substance is a carotinoid.

6. The process in accordance with claim 1, wherein said oxygen-sensitive, oil-soluble substance is an aroma.

* * * * *